US00PP24397P2

(12) United States Plant Patent
Hammett

(10) Patent No.: US PP24,397 P2
(45) Date of Patent: Apr. 22, 2014

(54) *DAHLIA* PLANT NAMED 'MYSTIC WONDER'

(50) Latin Name: *Dahlia variabilis*
Varietal Denomination: MYSTIC WONDER

(76) Inventor: Keith Hammett, Auckland (NZ)

( * ) Notice: Subject to any disclaimer, the term of this patent is extended or adjusted under 35 U.S.C. 154(b) by 0 days.

(21) Appl. No.: 13/385,714

(22) Filed: Mar. 2, 2012

Related U.S. Application Data

(60) Provisional application No. 61/465,517, filed on Mar. 21, 2011.

(51) Int. Cl.
*A01H 5/00* (2006.01)

(52) U.S. Cl.
USPC ..... Plt./321

(58) Field of Classification Search
USPC ..... Plt./321
See application file for complete search history.

*Primary Examiner* — Kent L Bell

(57) ABSTRACT

A new cultivar of *Dahlia* named 'MYSTIC WONDER' that is distinguishable by a compact rounded habit, velvety textured rich red single type inflorescences with dark central discs, glossy mahogany-black foliage and dark purple-brown stems. In combination these traits set 'MYSTIC WONDER' apart from all other existing varieties of *Dahlia* known to the inventor.

2 Drawing Sheets

Genus: *DAHLIA*.
Species: *variabilis*.
Denomination: 'MYSTIC WONDER'.

BACKGROUND OF THE INVENTION

This application claims the benefit of priority under 35 U.S.C. 119(e) of U.S. Provisional Application No. 61/465,517 filed on Mar. 21, 2011 entitled *DAHLIA* plant named 'MYSTIC WONDER'.

The present invention relates to a new and distinct cultivar of *dahlia* grown for use in mixed combinations, beds and the landscape. The new invention is known botanically as *Dahlia variabilis* and will be referred to hereinafter by the cultivar name 'MYSTIC WONDER'. The specific epithet *variabilis* represents a hybrid seedling line that came from crossing various original wild species in the early 1800's, and refers to the species' wide range of inflorescence color and shapes. *Dahlia* is in the family Compositae. The inflorescence of 'MYSTIC WONDER' is a "single" form blossom and exhibits a single row of ray florets surrounding a central cluster of disk florets.

'MYSTIC WONDER' was selected as a seedling that resulted from the controlled cross-pollination carried out by the inventor in a cultivated area of Auckland, New Zealand. The breeding began in 1995 by crossing an individual plant *Dahlia variabilis* Selection '71509/01' (unpatented) as the female parent and an individual of *Dahlia variabilis* 'ZONE TEN' (U.S. Plant Pat. No. 19,885) as the male parent. Seed was collected from the female parent and coded as 71762/01, then sown with the intention of making a selection from the seedlings that resulted.

'MYSTIC WONDER' was selected in 2008 based on the criteria of leaf color, leaf shape, plant height, self supporting plants, single type of inflorescence and inflorescence color. Selection was conducted by the inventor, in Auckland, New Zealand. The unique traits that distinguish 'MYSTIC WONDER' from other varieties of *Dahlia* known to the inventor are glossy mahogany-black divided leaves and profusions of rich velvety textured rich red inflorescences with dark central discs. 'MYSTIC WONDER' is distinguishable from the parents predominantly by inflorescence and foliage color. The inflorescences of Selection '71509/01' are striped and mauve in color. The inflorescences of 'ZONE TEN' (U.S. Plant Pat. No. 19,885) are striped and mauve in color, the plant is shorter in height and the foliage is less divided.

'MYSTIC WONDER' exhibits a compact rounded habit, velvety textured rich red inflorescences with dark central discs, glossy mahogany-black foliage and dark purple-brown stems. The large single type inflorescences bloom in summer and fall. Cultural conditions include full sun, regular water and rich well-draining potting soil. 'MYSTIC WONDER' is hardy to USDA Zone 9 and grows to 79 cm in height and 61 cm in width at maturity.

The variety of *Dahlia* which is considered by the inventor to most closely resemble 'MYSTIC WONDER' is *Dahlia* 'MYSTIC ENCHANTMENT' (U.S. Plant Pat. No. 23,332). The inflorescence of 'MYSTIC ENCHANTMENT' is scarlet while the inflorescence of 'MYSTIC WONDER' is a rich velvety textured red. The inflorescences of 'MYSTIC ENCHANTMENT' are larger in size than 'MYSTIC WONDER'. 'MYSTIC ENCHANTMENT' has a taller and more compact habit than 'MYSTIC WONDER'.

The first asexual reproduction of 'MYSTIC WONDER' was conducted in 2008 in Auckland, New Zealand. The method of asexual propagation utilized was softwood cuttings from the tuber in year two and tissue culture thereafter. Since that time under careful observation, the distinguishing characteristics have been determined stable, uniform, and to be reproduced true to type in subsequent generations of asexual propagation.

SUMMARY OF THE INVENTION

The following traits have been repeatedly observed and represent the distinguishing characteristics of the new *Dahlia* cultivar named 'MYSTIC WONDER'. These traits in combination distinguish 'MYSTIC WONDER' from all other existing varieties of *Dahlia* known to the inventor. 'MYSTIC WONDER' has not been tested under all possible conditions and phenotypic differences may be observed with variations in environmental, climatic, and cultural conditions, however, without any variance in genotype.

1. 'MYSTIC WONDER' exhibits compact rounded habit.
2. 'MYSTIC WONDER' exhibits glossy mahogany-black divided leaves and dark purple-brown stems.
3. 'MYSTIC WONDER' is grown for use in mixed combinations, beds and the landscape.
4. 'MYSTIC WONDER' exhibits large velvety textured rich red single type inflorescences with dark central discs.
5. 'MYSTIC WONDER' blooms summer and fall.
6. 'MYSTIC WONDER' grows to 79 cm in height and 61 cm in width at maturity
7. 'MYSTIC WONDER' is hardy to USDA Zone 9.

BRIEF DESCRIPTION OF THE DRAWINGS

The accompanying color drawings labeled

The drawing labeled FIG. 1 depicts the entire plant in bloom.

The drawing labeled FIG. 2 depicts a close-up view of an inflorescence.

Figure 1:
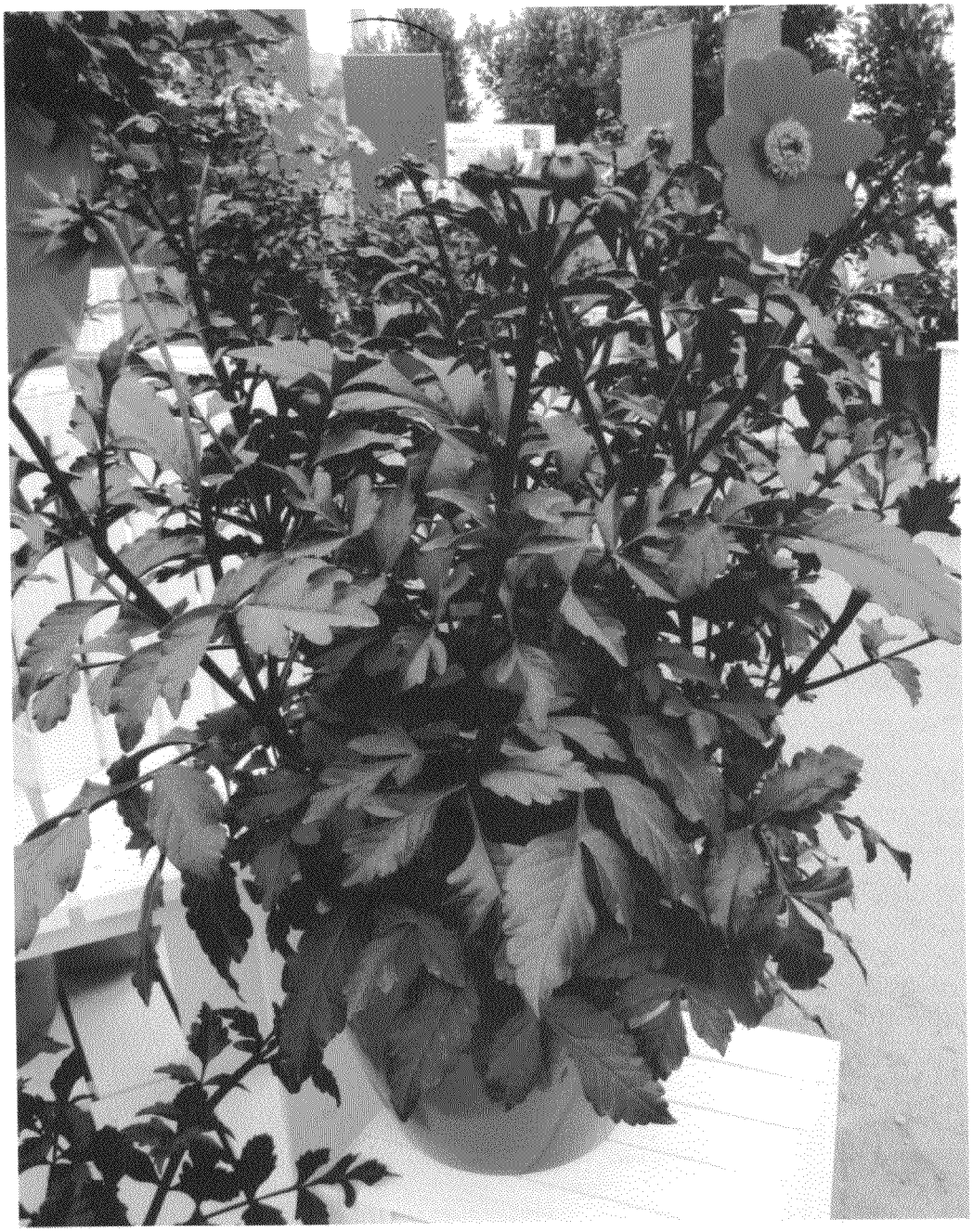
FIG. 1 and FIG. 2 illustrate the overall appearance of 'MYSTIC WONDER' showing the colors as true as is reasonably possible to obtain in colored reproductions of this type. Colors in the photographs may differ from the color values cited in the detailed botanical description, which accurately describes the actual colors of 'MYSTIC WONDER'.
Figure 2:
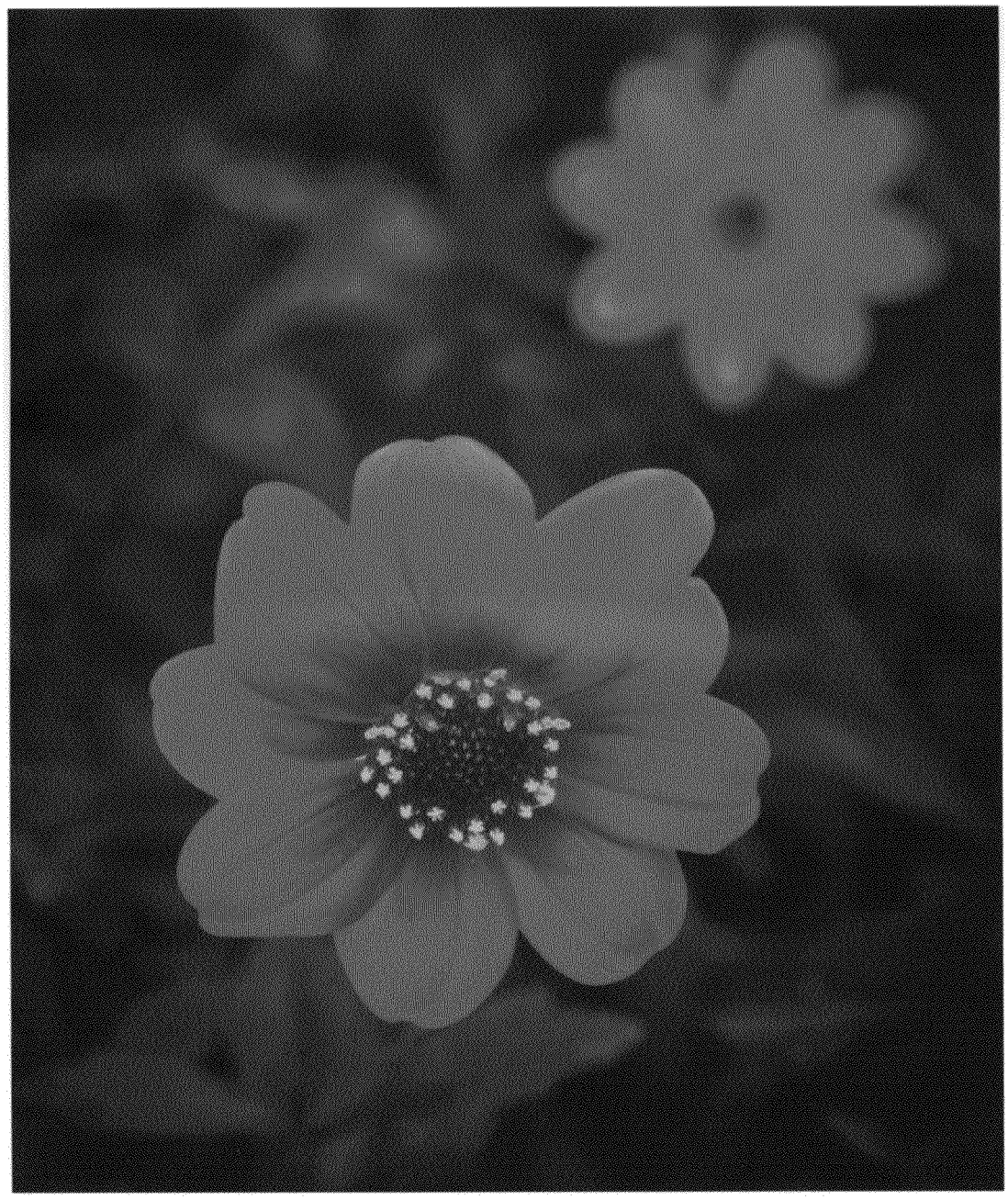

The drawings were made using conventional techniques and although inflorescence and foliage color may appear different from actual color due to light reflectance, they are as accurate as possible by conventional photography.

BOTANICAL DESCRIPTION OF THE PLANT

The following is a detailed botanical description of the new *Dahlia* cultivar named 'MYSTIC WONDER'. Observations, measurements, values and comparisons were collected in Santa Barbara, Calif. from a 9 month old plant grown in the landscape. Color determinations were made in accordance with The 2007 Royal Horticultural Society Colour Chart from London England, except where general color terms of ordinary dictionary significance are used. Growing requirements are similar to the species.

Botanical classification: *Dahlia variabilis* 'MYSTIC WONDER'.

Family: Compositae.

Genus: *DAHLIA*.

Species: *variabilis*.

Denomination: 'MYSTIC WONDER'.

Common name: *Dahlia*.

Parentage: *Dahlia variabilis* 'MYSTIC WONDER' is a seedling that resulted from the controlled cross-pollination of the following parents:

*Female parent.*—*Dahlia variabilis* Selection '71509/01' (unpatented).

*Male parent: Dahlia variabilis* 'ZONE TEN' (U.S. Plant Pat. No. 19,885).

Propagation method: Tissue culture.

Rooting system: Fine and fibrous.

Vigor: Vigorous.

Habit: Upright habit.

Use: For use in mixed combinations, beds and the landscape.

Type: Perennial.

Dimensions at maturity (one growing season): 79 cm in height and 61 cm in width.

Cultural requirements: Grow in full sun with regular water, and well-draining potting soil.

Pest susceptibility: Susceptible to aphids.

Disease susceptibility: Susceptible to mildew in highly humid conditions.

Hardiness: USDA Zone 9.

Stem:

*Color.*—N187A.

*Shape.*—Cylindrical.

*Dimensions.*—Length, 50 cm; diameter, 1.5 cm at base of stem, 0.7 cm below uppermost leaf.

*Surface.*—Glabrous.

*Internode length* (*average*).—12 cm.

Foliage: The foliage of 'MYSTIC ENCHANTMENT' is consistently mahogany-black when grown in full sun. Any part of the plant which is in shade, including the shade of other plant parts, turns olive-green in color, typically in the range 147A to 152A. This coloration is reversible such that the olive-green foliage returns to mahogany-black when exposed or re-exposed to full sun. All the color readings in the botanical description are taken from foliage and leaf parts growing in full sun.

Type: Evergreen.

*Leaf arrangement.*—Opposite.

*Leaf division.*—Occasionally simple, predominantly compound as plant develops and matures. The compound leaf structure is very evident in a mature plant.

Simple leaves:

*Leaf dimensions* (*average*).—10 cm-15 cm in length and 5 cm-6 cm in width.

*Leaf color* (*adaxial surface*).—Ranges between N186A and 200A.

*Leaf color* (*abaxial surface*).—147B.

*Margin.*—Ciliate and pinnatisect.

*Leaf shape.*—Hastate.

*Leaf base.*—Attenuate.

*Leaf apex.*—Apiculate.

*Leaf venation pattern.*—Pinnate.

*Vein color* (*abaxial and adaxial surfaces*).—N137D.

*Vein midrib* (*abaxial surface only*).—Lightly pubescent. Hairs, 1 mm long, fine, light gray.

*Leaf surfaces* (*abaxial surfaces*).—Slightly puberulent.

*Leaf surfaces* (*adaxial surfaces*).—Glabrous.

*Leaf attachment.*—Petiolate.

*Leaf fragrance.*—None observed.

*Petiole shape.*—Sulcate.

*Petiole dimensions.*—0.5 cm to 2 cm in length and 3-4 mm in width.

*Petiole color.*—N187A.

Compound leaves:

*Division.*—Bipinnately compound consisting of two pairs of trilobed lateral leaflets and one trilobed terminal leaflet.

*Compound leaf dimensions* (*average*).—24 cm in length and 22 cm in width.

*Leaflet dimensions.*—First pair (nearest stem) of lateral leaflets: Length 10.5 cm, width 6.5 cm. Second pair of lateral leaflets: Length 7 cm, width 3 cm. Terminal leaflet: Length 7 cm, width 3 cm.

*Leaflet attachment.*—First pair (nearest stem) of lateral leaflets: Petiolule. Second pair of lateral leaflets: Sessile to rachis. Terminal leaflet: Sessile to rachis.

*Leaflet shape, base, apex, margin, color, venation, surface are all identical for lateral leaflets and terminal leaflets as follows.*—Base: Attenuate. Apex: Apiculate. Margin: Ciliate and pinnatisect. Color (both surfaces): 203A. Venation pattern: Pinnate. Leaf venation pattern: Pinnate. Vein color (abaxial and adaxial surfaces): N137D. Vein midrib (abaxial surface only): Lightly pubescent. Hairs, 1 mm long, fine, light gray. Leaf surfaces (abaxial surfaces): Slightly puberulent. Leaf surfaces (adaxial surfaces): Glabrous. Leaf attachment: Petiolate.

*Compound leaf petiole (from stem to first pair of leaflets)*.—Shape: Sulcate. Dimensions: 0.5 cm to 2 cm in length and 3-4 mm in width. Color: Adaxial surface: 187B, abaxial surfaces: 187B with streaks of 147C. Surfaces: Glabrous.

*Compound leaf rachis (from first pair of leaflets to base of terminal leaflet)*.—Shape: Sulcate with central midrib. Dimensions: 10 cm in length, 3 mm in width. Color: Adaxial surface: 187B, abaxial surfaces: 187B with streaks of 147C. Surfaces: Glabrous.

*First pair of leaflet petiolules.*—Shape: Sulcate. Dimensions: 3 cm in length, 1.25 mm in width. Color: Adaxial surface: 187B, abaxial surfaces: 187B with streaks of 147C. Surfaces: Glabrous.

Inflorescence:

*Inflorescence type.*—Terminal: Inflorescence classified as "single" form, with single row of ray florets surrounding a central cluster of disk florets.

*Aspect.*—Facing upward and outward.

*Inflorescence quantity.*—15-20 per 2-litre container plant.

*Dimensions of inflorescence (average).*—9.5 cm in diameter and 2.5 cm in depth.

*Inflorescence shape.*—Radiate with center disk.

*Blooming seasons.*—Summer and fall.

*Peduncle.*—Dimensions (average): 20 cm in length and 0.3-0.4 cm in diameter. Shape: Cylindrical. Surface: Glabrous. Color: N187A.

*Bud.*—Shape: Oblate. Dimensions (average): 1.2 cm in height and 1.5 cm in diameter. Surface: Glabrous. Appearance: Semi-glossy. Color: 153D when newly formed, developing longitudinal streaks 187C and becoming uniformly 187B immediately prior to opening. Apex: Obtuse. Base: Truncate.

*Ray florets.*—Quantity per inflorescence: 8-10. Dimensions (average): 4.50 cm in length and 3.2 cm in width. Shape: Obovate. Apex: Obtuse with minute acute tip. Base: Cuneate. Margin: Entire. Surface (adaxial): Glabrous. Surface (abaxial): Matte. Arrangement: Radiate. Color (both surfaces): 45B. Veins (both surfaces): Fine and barely color distinguishable from 45B, becoming dark 187A towards base of ray floret. Vein pattern: Parallel.

*Disk florets.*—Disk diameter: 2.0 cm-2.2 cm. Quantity of disk florets: 50-60 per inflorescence. Corolla: Tubular, sympetalous with 5 lobes, apices acute. Corolla dimensions: 10 mm in length and 2 mm in diameter. Corolla surface (both surfaces): Glabrous. Corolla color: Ranges between N35A and 53A. Receptacle dimensions: 0.7 cm in depth and 2.5 cm in diameter. Receptacle surface: Glabrous. Receptacle color: 53A.

*Phyllary.*—Inner phyllary: Number: 8. Shape: Elongated ovate. Dimensions: 2.0-2.5 cm in length and 8 mm-11 mm in width. Color (adaxial and abaxial surfaces): 151D except 139C at base. Texture: Scarious, waxy. Appearance: Translucent. Apex: Rounded to subacute. Base: Truncate. Margin: Entire. Surface (adaxial and abaxial): Glabrous. Outer phyllary: Number: 5 in number. Shape: Obovate. Dimensions: 1.50 cm in length and 0.8 cm in width. Color (adaxial and abaxial surfaces): 200A. Form: Reflexed. Apex: Obtuse. Base: Truncate. Margin: Entire. Surface (adaxial): Glabrous, glossy, ribbed. Approximately 10 longitudinal ribs 0.5-0.8 mm apart. Surface (abaxial): Glabrous, glossy, smooth.

*Self-cleaning or persistent.*—Self-cleaning.

Reproductive organs:

Androecium: Present on disk florets only.

*Stamens.*—5 in number.

*Stamen attachment.*—Filament adnate to ventral surface of corolla.

*Stamen length.*—6 mm in length.

*Stamen color.*—169A.

*Anther.*—Connate.

*Anther color.*—169A.

*Pollen.*—Present.

*Quantity.*—Large amount.

*Pollen color.*—17A.

Gynoecium: Present on ray florets and disc florets.

*Pistil.*—One present.

*Pistil length.*—12 mm in length.

*Stigma dimensions.*—3 mm in length and 0.5 mm in width.

*Stigma form.*—Plumose.

*Stigma color.*—N169A.

*Stigma shape.*—Bifurcate.

*Ovary position.*—Inferior.

*Ovary color.*—150D.

*Ovary shape.*—Rotund.

*Ovary dimensions.*—2 mm in width and 3 mm in height.

Seed: Seed has not been found during repeated observations.

The invention claimed is:

1. A new and distinct cultivar of *Dahlia* plant named 'MYSTIC WONDER' as described and illustrated herein.

* * * * *